US008461331B2

(12) United States Patent  (10) Patent No.: US 8,461,331 B2
Helmreich et al.  (45) Date of Patent: Jun. 11, 2013

(54) METHOD FOR THE PRODUCTION OF 3,6-DIHYDRO-L, 3, 5-TRIAZINE DERIVATIVES FROM METFORMIN AND PARALDEHYDE DERIVATIVES

(75) Inventors: Matthias Helmreich, Heidelberg (DE); Mike Brandner, Gross-Gerau (DE)

(73) Assignee: Poxel SAS, Lyons (FR)

( * ) Notice: Subject to any disclaimer, the term of this patent is extended or adjusted under 35 U.S.C. 154(b) by 218 days.

(21) Appl. No.: 12/735,608

(22) PCT Filed: Jan. 15, 2009

(86) PCT No.: PCT/EP2009/000212
§ 371 (c)(1),
(2), (4) Date: Dec. 6, 2010

(87) PCT Pub. No.: WO2009/095159
PCT Pub. Date: Aug. 6, 2009

(65) Prior Publication Data
US 2011/0118463 A1  May 19, 2011

(30) Foreign Application Priority Data
Feb. 2, 2008  (DE) .......................... 10 2008 007 314

(51) Int. Cl.
C07D 251/10 (2006.01)
A61K 31/53 (2006.01)
A61P 3/06 (2006.01)
A61P 3/10 (2006.01)

(52) U.S. Cl.
USPC ........... 544/204; 544/206; 544/208; 544/209; 514/245

(58) Field of Classification Search
USPC .......................... 544/182, 204, 206, 208, 209
See application file for complete search history.

(56) References Cited

U.S. PATENT DOCUMENTS

| 7,034,021 B2 * | 4/2006 | Moinet et al. ................. 514/245 |
| 2003/0109530 A1 | 6/2003 | Moinet |
| 2006/0154928 A1 | 7/2006 | Maeda |

FOREIGN PATENT DOCUMENTS

| EP | 1 574 503 | 9/2005 |
| WO | 01/55122 | 8/2001 |

OTHER PUBLICATIONS

Modest et al. J. Org. Chem., 21(1), 14-20, 1956.*
International Search Report for PCT/EP2009/000212, mailed Apr. 2, 2009.

* cited by examiner

Primary Examiner — Venkataraman Balasubramanian
(74) Attorney, Agent, or Firm — Nixon & Vanderhye P.C.

(57) ABSTRACT

Process for the preparation of compounds of the formula I

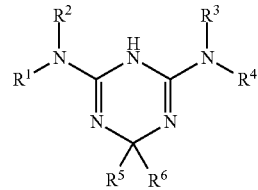

I in which
$R^1$, $R^2$, $R^3$, $R^4$, $R^5$ and $R^6$ have the meanings indicated in claim 1, which comprises the reaction of a compound of the formula II

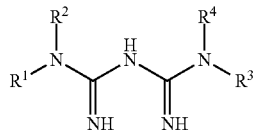

II in which
$R^1$, $R^2$, $R^3$, $R^4$ have the meanings indicated above, with a compound of the formula III

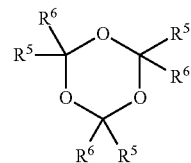

III in which
$R^5$, $R^6$ have the meanings indicated above.

8 Claims, No Drawings

METHOD FOR THE PRODUCTION OF 3,6-DIHYDRO-L, 3, 5-TRIAZINE DERIVATIVES FROM METFORMIN AND PARALDEHYDE DERIVATIVES

This application is the U.S. national phase of International Application No. PCT/EP2009/000212, filed 15 Jan. 2009 which designated the U.S. and claims priority to German Application No. 10 2008 007 314.8, filed 2 Feb. 2008, the entire contents of each of which are hereby incorporated by reference.

The invention relates to a process for the preparation of compounds of the formula I

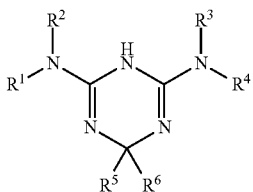

in which $R^1$, $R^2$ each, independently of one another, denote H or A, $R^3$, $R^4$ each, independently of one another, denote H, A, alkenyl having 2-6 C atoms, alkynyl having 2-6 C atoms, Ar or Het, $R^5$ and $R^6$ together also denote alkylene having 2, 3, 4 or 5 C atoms, $R^5$, $R^6$ each, independently of one another, denote H, A, $(CH_2)_nAr$, $(CH_2)_mOAr$, $(CH_2)_mOA$ or $(CH_2)_mOH$, $R^5$ and $R^6$ together also denote alkylene having 2, 3, 4 or 5 C atoms, in which one $CH_2$ group may be replaced by O, NH or NA and/or in which 1H atom may be replaced by OH, Ar denotes phenyl, naphthyl or biphenyl, each of which is unsubstituted or mono-, di- or trisubstituted by Hal, A, OA, OH, COOH, COOA, CN, $NH_2$, NHA, $NA_2$, $SO_2A$ and/or COA, Het denotes a mono-, bi- or tricyclic saturated, unsaturated or aromatic heterocycle having 1 to 4 N, O and/or S atoms, which may be unsubstituted or mono-, di- or trisubstituted by Hal, A, OH, OA, $NH_2$, $(CH_2)_nAr$, NHA, $NA_2$, COOH, COOA and/or =O (carbonyl oxygen), A denotes unbranched or branched alkyl having 1-10 C atoms, in which 1-7 H atoms may be replaced by F, or cyclic alkyl having 3-7 C atoms, Hal denotes F, Cl, Br or I, m denotes 1, 2, 3, 4, 5 or 6, n denotes 0, 1 or 2, and acid-addition salts thereof, which comprises the reaction of a compound of the formula II

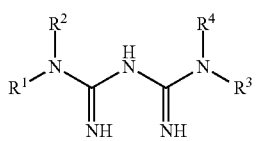

in which $R^1$, $R^2$, $R^3$, $R^4$ have the meanings indicated above, with a compound of the formula III

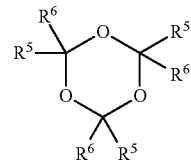

in which $R^5$, $R^6$ have the meanings indicated above.

Other processes for the preparation of compounds of the formula I are known from EP 1 250 328 B1.

The compounds of the formula I are useful in the treatment of diseases associated with insulin resistance syndrome.

Surprisingly, investigations in the course of the synthesis of dihydro-1,3,5-triazinamine derivatives showed that the compounds of the formula I can be obtained in at least comparable or higher yield compared with the prior art, where crucial advantages which may be mentioned here are a considerably shorter reaction time and fewer waste products. This consequently also means considerably lower energy consumption.

Thus, one molecule of water is liberated in the process according to the invention per molecule of compound of the formula I formed. In the prior-art process, two molecules of alcohol are liberated per molecule of compound of the formula I formed.

In particular, the compound 4-amino-3,6-dihydro-2-dimethylamino-6-methyl-1,3,5-triazine is prepared by the process according to the invention.

Above and below, the radicals $R^1$, $R^2$, $R^3$, $R^4$, $R^5$, $R^6$ have the meanings indicated for the formula I, unless expressly indicated otherwise.

Formula I also encompasses the optically active forms (stereoisomers), such as the enantiomers.

Metformin as preferred starting material has the structure

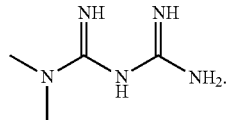

A denotes alkyl, which is unbranched (linear) or branched and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, further preferably, for example, trifluoromethyl.

A furthermore preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl. A very particularly preferably denotes methyl.

Cyclic alkyl (cycloalkyl) preferably denotes cyclopropyl, cyclobutyl, cyclopentyl, cyclohexyl or cycloheptyl.

Alkenyl has 2, 3, 4, 5 or 6 C atoms and preferably denotes vinyl or propenyl.

Alkynyl has 2, 3, 4, 5 or 6 C atoms and preferably denotes C≡CH or C≡C—$CH_3$.

Ar denotes, for example, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-aminophenyl, o-, m- or p-(N-methylamino)phenyl, o-, m- or p-(N-methylaminocarbonyl)-phenyl, o-, m- or p-methoxyphenyl, o-, m- or p-ethoxyphenyl, o-, m- or p-ethoxycarbonyl-phenyl, o-, m- or p-(N,N-dimethylamino) phenyl, o-, m- or p-(N-ethylamino)-phenyl, o-, m- or p-(N, N-diethylamino)phenyl, o-, m- or p-fluorophenyl, o-, m- or p-bromophenyl, o-, m- or p-chlorophenyl, o-, m- or p-(methylsulfonyl)phenyl, o-, m- or p-cyanophenyl, o-, m- or p-carboxyphenyl, o-, m- or p-methoxycarbonylphenyl, o-, m- or p-acetylphenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-amino-4-chloro-, 2-amino-3-chloro-, 2-amino-4-chloro-, 2-amino-5-chloro- or 2-amino-6-chlorophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-fluoro-4-methoxyphenyl, 3-amino-6-methylphenyl or 2,5-dimethyl-4-chlorophenyl.

Ar particularly preferably denotes phenyl, hydroxyphenyl or methoxyphenyl.

Irrespective of further substitutions, Het denotes, for example, 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, indazolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-[1,4-]oxazinyl, further preferably 1,3-benzodioxol-5-yl, 1,4-benzodioxan-6-yl, 2,1,3-benzothiadiazol-4- or -5-yl, 2,1,3-benzoxadiazol-5-yl or dibenzofuranyl.

The heterocyclic radicals may also be partially or fully hydrogenated. Irrespective of further substitutions, Het can thus, for example, also denote 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-,-4-, -5-, -6-,-7- or -8-isoquinolyl, 2-, 3-, 5-, 6-, 7- or 8-3,4-dihydro-2H-benzo-[1,4-]oxazinyl, further preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or -6-yl, 2,3-(2-oxomethylenedioxy)phenyl or also 3,4-dihydro-2H-1,5-benzodioxepin-6- or -7-yl, furthermore preferably 2,3-dihydrobenzofuranyl, 2,3-dihydro-2-oxofuranyl, 3,4-dihydro-2-oxo-1H-quinazolinyl, 2,3-dihydrobenzoxazolyl, 2-oxo-2,3-dihydrobenzoxazolyl, 2,3-dihydrobenzimidazolyl, 1,3-dihydroindolyl, 2-oxo-1,3-dihydroindolyl or 2-oxo-2,3-dihydrobenzimidazolyl.

Het preferably denotes piperidinyl, piperazinyl, pyrrolidinyl, morpholinyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, indolyl, benzo-[1,3-]dioxolyl, indazolyl or benzo-[2,1,3-]thiadiazolyl, each of which is unsubstituted or mono-, di- or trisubstituted by A, COOA, Hal and/or =O (carbonyl oxygen).

$R^1$, $R^2$ preferably denote A.
$R^3$, $R^4$ preferably denote H.
$R^5$ preferably denotes H.
$R^6$ preferably denotes A.
Very particularly preferably,
$R^1$, $R^2$ denote methyl,
$R^3$, $R^4$ denote H,
$R^5$ denotes H,
$R^6$ denotes methyl.

The compounds having the general formula (II) are biguanides, the synthesis of which is mastered by the average person skilled in the art. Some publications in which the synthesis of such compounds is described are cited by way of example (FR 1 537 604; FR 2 132 396; K. H. Slotta and R. Tschesche, Ber., 1929 (62b), 1398; S. L. Shapiro, V. A. Parrino, E. Rogow and L. Freedman, J. Org. Chem., 1959 (81), 3725; S. L. Shapiro, V. A. Parrino and L. Freedman, J. Org. Chem., 1959 (81), 3728 and S. L. Shapiro, V. A. Parrino and L. Freedman, J. Org. Chem., 1959 (81), 4636).

The reaction of the compounds II and III proceeds in a suitable polar solvent, such as, for example, alcohols, such as methanol, ethanol, isopropanol, n-propanol, n-butanol, isobutanol or tert-butanol; ethers, such as diethyl ether, diisopropyl ether, tetrahydrofuran (THF) or dioxane; glycol ethers, such as ethylene glycol monomethyl or monoethyl ether_ (methylglycol or ethylglycol), ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); esters, such as ethyl acetate, or mixtures of the said solvents.

Particular preference is given to isobutanol, furthermore ethanol and isopropanol.

Depending on the conditions used, the reaction time is between a few minutes and 14 days, particularly preferably between 3 and 12 hours; the reaction temperature is between about 50° and 150°, normally between 90° and 120°.

The reaction is carried out in the presence of an organic or inorganic acid. Thus, it is possible to use inorganic acids, for example sulfuric acid, nitric acid, hydrohalic acids, such as hydrochloric acid or hydrobromic acid, phosphoric acids, such as orthophosphoric acid, sulfamic acid, furthermore organic acids, in particular aliphatic, alicyclic, araliphatic, aromatic or heterocyclic mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, laurylsulfuric acid.

Also suitable are acidic cationic ion exchanger resins, such as, for example, the commercially available Dowex® or Amberlyst® resins. Very particular preference is given to p-toluenesulfonic acid, furthermore hydrochloric acid, methanesulfonic acid, sulfuric acid or camphorsulfonic acid, or acidic cationic ion exchanger resins, for example Dowex® 50, Amberlyst® 15 or Dowex® DR-2030.

A base of the formula I can be converted into the associated acid-addition salt using an acid, for example by reaction of equivalent amounts of the base and acid in an inert solvent, such as ethanol, with subsequent evaporation. Particularly suitable acids for this reaction are those which give physiologically acceptable salts. Thus, it is possible to use inorganic acids, for example sulfuric acid, nitric acid, hydrohalic acids, such as hydrochloric acid or hydrobromic acid, phosphoric acids, such as orthophosphoric acid, sulfamic acid, furthermore organic acids, in particular aliphatic, alicyclic, araliphatic, aromatic or heterocyclic mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethane-sulfonic acid, ethanedisulfonic acid, 2-hydroxyethanesulfonic acid, benzenesulfonic acid, p-toluenesulfonic acid, naphthalenemono- and -disulfonic acids, laurylsulfuric acid. Salts with physiologically unacceptable acids, for example picrates, can be used for the isolation and/or purification of the compounds of the formula I.

Above and below, all temperatures are given in ° C. In the following examples, "conventional work-up" means: if necessary, water is added, the pH is, if necessary, adjusted to values between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation.

Preparation of 4-amino-3,6-dihydro-2-dimethylamino-6-methyl-1,3,5-triazine hydrochloride Comparative Example A mixture of 250.2 g of metformin hydrochloride, 213.6 g of acetaldehyde diethyl acetal and 12.5 g of toluene-4-sulfonic acid monohydrate in 500 ml of isobutanol is heated under reflux for 40 hours. Some of the solvent is removed by distillation. The mixture is cooled to 10°, and the white precipitate is separated off, giving 224.7 g (77.4%) of 4-amino-3,6-dihydro-2-dimethylamino-6-methyl-1,3,5-triazine hydrochloride.

Example 1

A mixture of 1002.6 g of metformin hydrochloride, 359.1 g of paraldehyde and 51.6 g of toluene-4-sulfonic acid monohydrate in 2405.9 g of isobutanol is heated under reflux for 6 hours. Some of the solvent is removed by distillation. The mixture is cooled to 12°, and the white precipitate is separated off, giving 953.8 g (81.4%) of 4-amino-3,6-dihydro-2-dimethylamino-6-methyl-1,3,5-triazine hydrochloride.

Example 2

A mixture of 100.1 g of metformin hydrochloride, 36.5 g of paraldehyde and 4 g of Dowex DR-2030 in 237.8 ml of isobutanol is heated under reflux for 6 hours. The catalyst is subsequently filtered off, and some of the solvent is removed by distillation. The remainder of the solution is cooled to 10-15° C., and the white precipitate is separated off, giving 93.5 g (80.7%) of 4-amino-3,6-dihydro-2-dimethylamino-6-methyl-1,3,5-triazine hydrochloride.

The invention claimed is:

1. Process for the preparation of a compound of the formula I

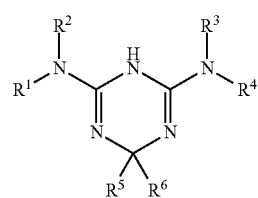

in which $R^1$, $R^2$ each, independently of one another, denote H or A,
$R^3$, $R^4$ each, independently of one another, denote H, A, alkenyl having 2-6 C atoms or alkynyl having 2-6 C atoms
$R^5$, $R^6$ each, independently of one another, denote H or A,
A denotes unbranched or branched alkyl having 1-10 C atoms, in which 1-7 H atoms may be replaced by F, or cyclic alkyl having 3-7 C atoms,
or an acid-addition salt thereof,
which comprises the reaction of a compound of the formula II

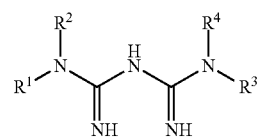

in which
$R^1$, $R^2$, $R^3$, $R^4$ have the meanings indicated above, with a compound of the formula III

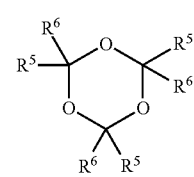

in which
$R^5$, $R^6$ have the meanings indicated above,
wherein the reaction is carried out in the presence of an organic or inorganic acid or an acidic cationic ion exchanger resin.

2. Process according to claim 1 where the reaction is carried out in the presence of para-toluenesulfonic acid or an acidic cationic ion exchanger resin.

3. Process according to claim 1, where the reaction is carried out in a polar solvent.

4. Process according to claim 1, where the reaction is carried out in isobutanol.

5. Process according to claim 1, for the preparation of a compound of the formula I
in which
$R^1$, $R^2$ denote A.

6. Process according to claim 1, for the preparation of a compound of the formula I
in which
$R^3$, $R^4$ denote H.

7. Process according to claim 1, for the preparation of a compound of the formula I
in which
$R^5$ denotes H,
$R^6$ denotes A.

8. Process according to claim 1, for the preparation of a compound of the formula I
in which
$R^1$, $R^2$ denote methyl,
$R^3$, $R^4$ denote H,
$R^5$ denotes H,
$R^6$ denotes methyl.

\* \* \* \* \*

UNITED STATES PATENT AND TRADEMARK OFFICE
CERTIFICATE OF CORRECTION

PATENT NO. : 8,461,331 B2  Page 1 of 1
APPLICATION NO. : 12/735608
DATED : June 11, 2013
INVENTOR(S) : Helmreich et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 345 days.

Signed and Sealed this
Eighth Day of September, 2015

Michelle K. Lee
*Director of the United States Patent and Trademark Office*